United States Patent [19]

Bodor et al.

[11] 4,268,441

[45] May 19, 1981

[54] PRODRUGS FOR IMPROVED BIOAVAILABILITY OF CERTAIN $\Delta^4$-3-KETOSTEROIDAL SEX HORMONES

[75] Inventors: Nicholas S. Bodor, Gainesville, Fla.; Kenneth B. Sloan, Eudora, Kans.

[73] Assignee: INTERx Research Corporation, Lawrence, Kans.

[21] Appl. No.: 57,324

[22] Filed: Jul. 13, 1979

Related U.S. Application Data

[63] Continuation-in-part of Ser. No. 886,589, Mar. 14, 1978, abandoned.

[30] Foreign Application Priority Data

Mar. 13, 1979 [AU] Australia .............................. 45084/79
Mar. 13, 1979 [CA] Canada .................................... 323352

[51] Int. Cl.³ ......................... A61K 31/58; C07J 33/00
[52] U.S. Cl. .................................. 260/239.5; 424/241

[58] Field of Search ...................... 424/241; 260/239.5

[56] References Cited

U.S. PATENT DOCUMENTS 4,069,322  1/1978  Bodor et al. ..................... 260/239.5

*Primary Examiner*—Elbert L. Roberts
*Attorney, Agent, or Firm*—Burns, Doane, Swecker & Mathis

[57] ABSTRACT

Transient, orally active thiazolidine type prodrug forms of conventional, natural and synthetic ketosteroidal sex hormones, e.g., of progesterone, testosterone, and the like, are disclosed. The subject compounds can be prepared by known methods, for example, by reacting the corresponding 3-keto or 3,20-diketo steroids with a thiazolidine-forming reagent such as an L-cysteine alkyl ester.

144 Claims, No Drawings

PRODRUGS FOR IMPROVED BIOAVAILABILITY OF CERTAIN Δ⁴-3-KETOSTEROIDAL SEX HORMONES

CROSS-REFERENCE TO RELATED APPLICATION

This application is a continuation-in-part of our earlier copending application Ser. No. 886,589, filed Mar. 14, 1978, now abandoned, assigned to the assignee hereof and hereby expressly incorporated by reference in its entirety and relied upon.

TECHNICAL FIELD OF THE INVENTION

The present invention relates to certain transient thiazolidine type prodrug derivatives of the natural and synthetic ketosteroidal sex hormones (e.g., of progesterone and testosterone), and, more especially, relates to those orally active prodrugs having the structural formulae:

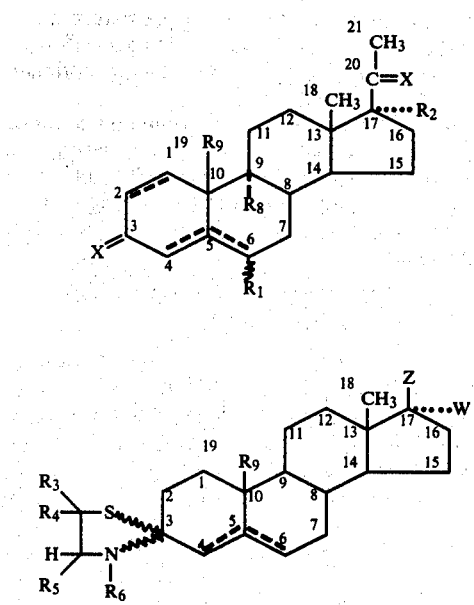

wherein each =X is =O or

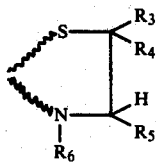

with the proviso that both =X's cannot at the same time be =O, albeit either one or both can comprise the depicted thiazolidine nucleus;

$R_1$ is H, $C_1$-$C_8$ alkyl or halogen (e.g., Cl, F, or Br);
$R_2$ is H, OH, OOCR$_7$, halogen or $C_1$-$C_{10}$ alkyl;
$R_3$ and $R_4$ may be the same or different and each is H or $C_1$-$C_8$ alkyl;
$R_5$ is H or —COOR$_7$;
$R_6$ is H, —COR$_7$ or —COOR$_7$, with the proviso that, when $R_6$ is H, the pharmaceutically acceptable acid addition salts, HQ, of the compounds (I) and (II) are also intended;
$R_7$ is H, $C_1$-$C_{20}$ alkyl, $C_2$-$C_{20}$ alkenyl, $C_5$-$C_7$ cycloalkyl, $C_5$-$C_7$ cycloalkyl-$C_6$-$C_{10}$ aryl, phenyl or $C_1$-$C_4$ alkyl-phenyl;
$R_8$ is H, Cl or F;
$R_9$ is H or $C_1$-$C_8$ alkyl;
$R_{10}$ is H, $C_1$-$C_8$ alkyl, $C_2$-$C_8$ alkenyl, CCl$_3$, CBr$_3$, phenyl, substituted phenyl (e.g., phenyl substituted with the substituents lower alkyl, halo, lower alkoxy, and the like) or $C_6H_5$—CH=CH—;
$R_{11}$ is H or COR$_7$;
Z is OH, OCOR$_7$ or

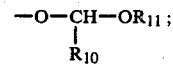

W is H, $C_1$-$C_{12}$ alkyl, $C_2$-$C_8$ alkenyl or $C_2$-$C_8$ alkynyl;

the dotted line at the 1(2)-position in Formula (I) indicates the optional presence of a double bond; and the dotted lines at the 4(5) and 5(6)-positions indicate the presence of a double bond at either the 4(5)- or the 5(6)-position.

The subject ketosteroidal prodrugs are orally active, are not rapidly metabolically deactivated, but are transient and will cleave upon administration of the active, basic steroid resulting in therapeutic concentrations and eliciting, albeit more efficiently and prolongedly, that same pharmacodynamic effect as would be elicited upon administration of a suitable dosage form of the known parent natural or synthetic sex hormone. The topic prodrugs thus are useful, inter alia, for oral contraception, as well as for all other applications for which the parent sex hormones are known to be of use.

For purposes of this specification, the term "prodrug" denotes a derivative of a known and proven prior art natural or synthetic sex hormone (e.g., progesterone, testosterone, and others of progestin or androgenic type), which derivative when administered to a warm-blooded animal, "cleaves" in such a manner as to release the proven drug form at its target site or sites of activity.

The term "transient" denotes enzymatic and/or chemical hydrolytic "cleavage" of the compounds of the instant invention in such a manner that the proven drug form (the conventional natural or synthetic sex hormone) is released, while the remaining "cleaved" moiety remains nontoxic and is metabolized in such a manner that nontoxic, metabolic products are produced.

Finally, the term "pharmaceutically acceptable acid addition salt" as used herein generally includes the nontoxic acid addition salts of selected compounds of Formulas (I) and (II), formed with nontoxic inorganic or organic acids. For example, the salts include those derived from inorganic acids such as hydrochloric, hydrobromic, sulfuric, sulfamic, phosphoric, nitric and the like; and the salts prepared from organic acids such as acetic, propionic, succinic, glycollic, stearic, latic, malic, tartaric, citric, ascorbic, pamoic, maleic, hydroxymaleic, phenylacetic, glutamic benzoic, salicylic, sulfanilic, fumaric, sulfonic, toluenesulfonic, and the like.

BACKGROUND OF THE PRIOR ART

The about 100 pharmacologically different products available for oral contraception are based on synthetic hormones, mostly as a fixed combination of an estrogen and a progestogen. The contraceptive action of these products is mediated principally via inhibition of ovulation, an effect mediated via specific macromolecular receptors. Evidence clearly shows the presence in human tissues of an estradiol-receptor, which does not bind progesterone, and of a progesterone-receptor which does not bind estrogens.

The synthetic hormones used as contraceptives act on the estradiol and progesterone target tissues. It is clear that the natural hormones, estradiol and progesterone, if delivered to the receptors, should bring the same contraceptive effect as the synthetic analogs, while possibly decreasing or eliminating the side effects accompanying the use of the current contraceptive formulations.

The estrogenic component used in the oral contraceptives (17 α-ethynyl estradiol or its 3-methyl ether) are admittedly responsible for thromboembolic phenomena, liver disturbances and impairment of carbohydrate metabolism. Although estradiol itself might induce abnormalities in liver function, the 17 α-ethynyl group certainly has additional effects.

Potency estimates of the various natural and synthetic sex hormones are generally obscured by the lack or inadequacy of the bioavailability and physiological availability studies. More detailed studies have been carried out only with the synthetic hormones used, although good bioavailability of estradiol from solution or in micronized forms has also been shown.

On the other hand, good bioavailability still does not necessarily mean high biological activity. Practically completely available (i.e., delivered to the bloodstream) drugs can have low physiological availability if they undergo conjugation and/or metabolism during the absorption process or during the first pass through the liver. These kinds of deactivation are expected to occur the fastest with natural substances, such as the natural sex hormones.

Indeed, inactivation of the natural estrogens in the intestines and in the liver occurs at such a rate that their oral efficacy is minimal as compared to the synthetic estrogens or when estradiol is administered parenterally.

The situation is quite similar in the case of progesterone, which undergoes fast and extensive metabolism in the liver after it is absorbed, the main metabolic pathway being the reduction of the α,β-unsaturated ketone and the 20-oxo group to pregnane-3α, 20-diol.

Both progesterone and estradiol are quite water insoluble substances. Thus, in order to deliver these natural hormones efficiently to the receptors, after oral administration, one has to solve two problems simultaneously:

(i) Assure complete dissolution of the material at the absorption site; and
(ii) Prevent premature metabolism-conjugation during absorption, and at least during the first pass through the liver.

Although various formulation techniques (deliver in solution, micronization, dilution with matrices, etc.) or physical-chemical approaches for increasing water solubility (complex formation), can certainly solve the first problem, to assure dissolution of the material, and consequently good absorption, but the major problem of fast deactivation of the active compounds cannot be influenced by such techniques.

BRIEF SUMMARY OF THE INVENTION

Accordingly, a primary object of the present invention is to provide certain orally available and active pro-drug forms of certain natural and synthetic sex hormones, which prodrugs, or transient derivatives, possess the capability of efficiently penetrating biological barriers of warm-blooded animals, especially the gastrointestinal wall, and which transient derivatives protect their respective parent molecules from rapid metabolic deactivation, e.g., first pass metabolism in the liver.

Another object of this invention is to provide certain steroidal prodrugs which will cleave following administration to the active, basic steroid, in therepeutic concentrations.

Yet another object of the invention is to provide certain steroidal prodrugs which are well absorbed and which elicit the pharmacodynamic responses of their parent molecules in a more efficient and more prolonged action.

Still another object of the invention is to provide a new class of oral contraceptives.

Another object of the invention is to provide certain steroidal prodrugs, e.g., of progesterone and testosterone, that not only are completely dissolved at the absorption site and are prevented from premature metabolism-conjugation during absorption, but also afford in vivo recovery of the basic hormone in the optimum fashion to exert its activity.

These and other objects are conveniently attained according to the invention by orally administering to a warm-blooded animal a therapeutically effective amount, e.g., a contraceptive amount, of any compound having either the structural formula (I) or the structural formula (II), supra.

DETAILED DESCRIPTION OF THE INVENTION

All of the compounds encompassed by formulae (I) and (II) essentially satisfy the objectives of the present invention. However, preferred compounds are the pro-drugs of the natural hormones, i.e., progesterone and testosterone, and compounds closely related thereto, which can be represented by the formula

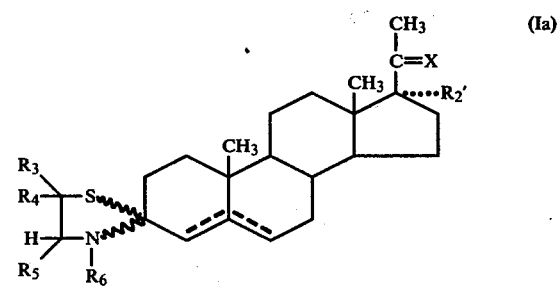

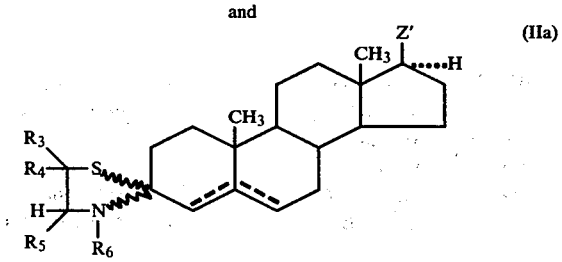

wherein $R_3$, $R_4$, $R_5$, $R_6$, X and the dotted lines are defined as hereinabove; $R_2'$ is H, OH, OCO ($C_1$–$C_{20}$ alkyl) or OCO ($C_1$–$C_4$ alkyl)-phenyl; and Z' is OH, OCO ($C_1$–$C_{20}$ alkyl) or OCO ($C_1$–$C_4$ alkyl)-phenyl. Compounds of formulae (Ia) and (IIa) wherein $R_6$ is hydrogen and/or wherein the double bond is in the 4-position are particularly preferred. Especially desirable compounds encompassed by the present invention can be represented by the formulae

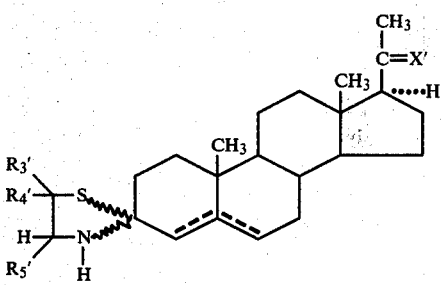

and

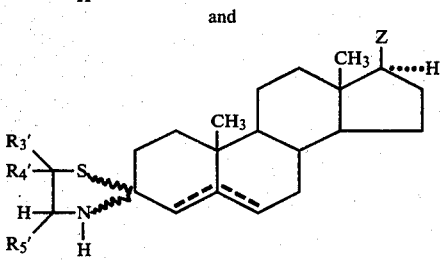

wherein $R_3'$ and $R_4'$ are each H or methyl; $R_5'$ is H or —$COOR_7'$ wherein $R_7'$ is H, $C_1$–$C_{20}$ alkyl or benzyl; =X' is =O or

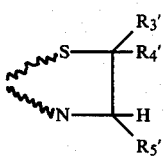

wherein $R_3'$, $R_4'$ and $R_5'$ are defined as above; Z' is OH, —OCO ($C_1$–$C_{20}$ alkyl) or —OCO ($C_1$–$C_4$ alkyl)-phenyl; and the dotted lines are as hereinbefore defined. Most especially preferred compounds of the invention can be considered to be derived from progesterone or testosterone and an L-cysteine alkyl ester or hydrochloride salt thereof wherein the alkyl group preferably contains 1 to 12 carbon atoms. Preferred specific embodiments of the present invention are the selected compounds set forth immediately below:

(1) 17β-(4″-Ethoxycarbonyl-2″-methyl-1″,3″-thiazolidin-2″-yl)-4-androstene-3-spiro-2′-(4′-ethoxycarbonyl-1′,3′-thiazolidine) and the corresponding $\Delta^{5(6)}$ compound;

(2) 17β-(4″-Butyloxycarbonyl-2″-methyl-1″,3″-thiazolidin-2″-yl)-4-androstene-3-spiro-2′-(4′-butyloxycarbonyl-1′,3′-thiazolidine) and the corresponding $\Delta^{5(6)}$ compound;

(3) 17β-(4″-Hexyloxycarbonyl-2″-methyl-1″,3″-thiazolidin-2″-yl)-4-androstene-3-spiro-2′-(4′-hexyloxycarbonyl-1′,3′-thiazolidine) and the corresponding $\Delta^{5(6)}$ compound;

(4) 17β-(4″-Decyloxycarbonyl-2″-methyl-1″,3″-thiazolidin-2″-yl)-4-androstene-3-spiro-2′-(4′-decyloxycarbonyl-1′,3′-thiazolidine) and the corresponding $\Delta^{5(6)}$ compound;

(5) 17β-(4″-tert-Butyloxycarbonyl-2″-methyl-1″,3″-thiazolidin-2″-yl)-4-androstene-3-spiro-2′-(4′-tert-butyloxycarbonyl-1′,3′-thiazolidine) and the corresponding $\Delta^{5(6)}$ compound;

(6) 17β-(4″-Benzyloxycarbonyl-2″-methyl-1″,3″-thiazolidin-2″-yl)-4-androstene-3-spiro-2′-(4′-benzyloxycarbonyl-1′,3′-thiazolidine) and the corresponding $\Delta^{5(6)}$ compound;

(7) 17β-(4″-Isopropyloxycarbonyl-2″-methyl-1″,3″-thiazolidin-2″-yl)-4-androstene-3-spiro-2′-(4′-isopropyloxycarbonyl-1′,3′-thiazolidine) and the corresponding $\Delta^{5(6)}$ compound;

(8) 4-and 5-Pregnene-3-spiro-2′-(4′-ethoxycarbonyl-1′,3′-thiazolidine)-20-one;

(9) 4-and 5-Pregnene-3-spiro-2′-(4′-butyloxycarbonyl-1′,3′-thiazolidine)-20-one;

(10) 4- and 5-Pregnene-3-spiro-2′-(4′-hexyloxycarbonyl-1′,3′-thiazoline)-20-one;

(11) 4-and 5-Pregnene-3-spiro-2′-(4′-decyloxycarbonyl-1′,3′-thiazolidine)-20-one;

(12) 4- and 5-Pregnene-3-spiro-2′-(4′-tert-butyloxycarbonyl-1′,3′,-thiazolidine)-20-one;

(13) 4- and 5-Pregnene-3-spiro-2′-(4′-benzyloxycarbonyl-1′,3′-thiazolidine)-20-one;

(14) 4- and 5-Pregnene-3-spiro-2′-(4′-isopropyloxycarbonyl-1′,3′-thiazolidine)-20-one;

(15) 17β-(4″-Ethoxycarbonyl-2″,5″,5″-trimethyl-1″,3″-thiazolidin-2″-yl)-4-androstene-3-spiro-2′-(4′-ethoxycarbonyl-5′,5′-dimethyl-1′,3′-thiazolidine) and the corresponding $\Delta^{5(6)}$ compound;

(16) 17β-(4″-Hexyloxycarbonyl-2″,5″,5″-trimethyl-1″,3″-thiazolidin-2″-yl)-4-androstene-3-spiro-2′-(4′-hexyloxycarbonyl-5′,5′-dimethyl-1′,3′-thiazolidine) and the corresponding $\Delta^{5(6)}$ compound;

(17) 17β-(4″-Butyloxycarbonyl-2″,5″,5″-trimethyl-1″,3″-thiazolidin-2″-yl)-4-androstene-3-spiro-2′-(4′-butyloxycarbonyl-5′,5′-dimethyl-1′,3′-thiazolidine) and the corresponding $\Delta^{5(6)}$ compound;

(18) 6α-Chloro-17β-(4″-ethoxycarbonyl-2″-methyl-1″,3″-thiazolidin-2″-yl)-4-androstene-3-spiro-2′-(4′-ethoxycarbonyl-1′,3′-thiazolidine) and the corresponding $\Delta^{5(6)}$ compound;

(19) ∫β-(4″-Butyloxycarbonyl-2″-methyl-1″,3″-thiazolidin-2″-yl)-6α-chloro-4-androstene-3-spiro-2′-(4′-butyloxycarbonyl-1′,3′-thiazolidine) and the corresponding $\Delta^{5(6)}$ compound;

(20) 6α-Chloro-17β-(4″-hexyloxycarbonyl-2″-methyl-1″,3″-thiazolidin-2″-yl)-4-androstene-3-spiro-2′-(4′-hexyloxycarbonyl-1′,3′-thiazolidine) and the corresponding $\Delta^{5(6)}$ compound;

(21) 17α-Acetyloxy-17β-(4″-ethoxycarbonyl-2″-methyl-1″,3″-thiazolidin-2″-yl)-6α-methyl-4-androstene-3-spiro-2′-(4′-ethoxycarbonyl-1′,3′-thiazolidine) and the corresponding $\Delta^{5(6)}$ compound;

(22) 17α-Acetyloxy-17β-(4″-butyloxycarbonyl-2″-methyl-1″,3″-thiazolidin-2″-yl)-6α-methyl-4-androstene-3-spiro-2′-(4′-butyloxycarbonyl-1′,3′-thiazolidine) and the corresponding $\Delta^{5(6)}$ compound;

(23) 17α-Acetyloxy-17β-(4″-hexyloxycarbonyl-2″-methyl-1″,3″-thiazolidin-2″-yl)-6α-methyl-4-androstene-3-spiro-2′-(4′-hexyloxycarbonyl-1′,3′-thiazolidine) and the corresponding $\Delta^{5(6)}$ compound;

(24) 17α-Acetyloxy-17β-(4″-ethoxycarbonyl-2″-methyl-1″,3″-thiazolidin-2″-yl)-9α-fluoro-4-androstene-3-spiro-2′-(4′-ethoxycarbonyl-1′,3′-thiazolidine) and the corresponding $\Delta^{5(6)}$ compound;

(25) 17α-Acetyloxy-17β-(4″-butyloxycarbonyl-2″-methyl-1″,3″-thiazolidin-2″-yl)-9α-fluoro-4-androstene-3-spiro-2′-(4′-butyloxycarbonyl-1′,3′- thiazolidine) and the corresponding $\Delta^{5(6)}$ compound;

(26) 17α-Acetyloxy-9α-fluoro-17β-(4''-hexyloxycarbonyl-2''-methyl-1'',3''-thiazolidin-2''-yl)-4-androstene-3-spiro-2'-(4'-hexyloxycarbonyl-1',3'-thiazolidine) and the corresponding $\Delta^{5(6)}$ compound;

(27) 17α-Acetyloxy-6α-methyl-4-pregnene-3-spiro-2'-(4'-ethoxycarbonyl-1',3'-thiazolidine)-20-one and the corresponding $\Delta^{5(6)}$ compound;

(28) 17α-Acetyloxy-6α-methyl-4-pregnene-3-spiro-2'-(4'-hexyloxycarbonyl-1',3'-thiazolidine)-20-one and the corresponding $\Delta^{5(6)}$ compound;

(29) 17α-Acetyloxy-6α-methyl-4-pregnene-3-spiro-2'-(4'-isopropyloxycarbonyl-1',3'-thiazolidine)-20-one and the corresponding $\Delta^{5(6)}$ compound;

(30) 17β-[3'',4''-di(Ethoxycarbonyl)-2''-methyl-1'',3''-thiazolidin-2''-yl]-4-androstene-3-spiro-2'-[3',4'-di(ethoxycarbonyl)-1',3'-thiazolidine]and the corresponding $\Delta^{5(6)}$ compound;

(31) 17β-(4''-Carboxy-2'',5'',5''-trimethyl-1'',3''-thiazolidin-2''-yl)-4-androstene-3-spiro-2'-(4'-carboxy-5',5'-dimethyl-1',3'-thiazolidine) and the corresponding $\Delta^{5(6)}$ compound;

(32) 17α-Ethynyl-4-and 17α-ethynyl-5-androstene-3-spiro-2'-(4'-ethoxycarbonyl-1',3'-thiazolidine)-17β-ol;

(33) 17α-Ethynyl-19-nor-4-and 17α-ethynyl-19-nor-5-androstene-3-spiro-2'-(4'-ethoxycarbonyl-1',3'-thiazolidine)-17β-ol;

(34) 4- and 5-Androstene-3-spiro-2'-(4'-carboxy-1',3'-thiazolidine)-17β-ol;

(35) 4-and 5-Androstene-3-spiro-2'-(4'-ethoxycarbonyl-1',3'-thiazolidine)-17β-ol;

(36) 4-and 5-Androstene-3-spiro-2'-(4'-hexyloxycarbonyl-1',3'-thiazolidine)-17β-ol;

(37) 4-and 5-Androstene-3-spiro-2'-(4'-butyloxycarbonyl-5',5'-dimethyl-1',3'-thiazolidine)-17β-ol;

(38) 4- and 5-Androstene-3-spiro-2'-(4'-ethoxycarbonyl-1',3'-thiazolidine)-17β-ol 17-propionate;

(39) 19-Nor-4-and 19-nor-5-androstene-3-spiro-2'-(4'-ethoxycarbonyl-1',3'-thiazolidine)-17β-ol 17-propionate;

(40) 19-Nor-4-and 19-nor-5-androstene-3-spiro-2'-(4'-ethoxycarbonyl-1',3'-thiazolidine)-17β-ol 17-adamantyl carboxylate;

(41) 19-Nor-4-and 19-nor-5-androstene-3-spiro-2'-(4'-ethoxycarbonyl-1',3'-thiazolidine)-17β-ol 17-phenylpropionate;

(42) 4-and 5-Androstene-3-spiro-2'-(4'-ethoxycarbonyl-5',5'-dimethyl-1',3'-thiazolidine)-17β-ol;

(43) 17β-Propionyloxy-4-and 17β-propionyloxy-5-androstene-3-spiro-2'-(4'-ethoxycarbonyl-1',3'-thiazolidine);

(44) 17β-(4''-Methoxycarbonyl-2''-methyl-1'',3''-thiazolidin-2''-yl)-4-androstene-3-spiro-2'-(4'-methoxycarbonyl-1',3'-thiazolidine) and the corresponding $\Delta^{5(6)}$ compound;

(45) 17β-Propionyloxy-5-androstene-3-spiro-2'-(1',3'-thiazolidine) and the corresponding $\Delta^{4}$ compound; and

(46) 5-Pregnene-3-spiro-2'-(1',3'-thiazolidine)-20-one and the corresponding $\Delta^{4}$ compound.

The compounds of the present invention can be conveniently prepared by known methods, for example, the methods described in U.S. Pat. No. 4,069,322. Most conveniently, preparation involves contacting a compound corresponding to formula (I) but containing keto groups at both the 3- and 20-positions, or a compound corresponding to formula (II) containing a 3-keto group, with a reagent of the formula

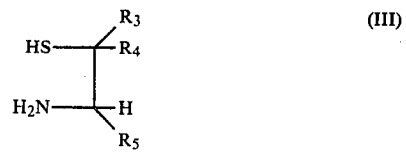

wherein $R_3$, $R_4$ and $R_5$ are as hereinbefore defined. The reaction is conducted in the presence of a suitable organic solvent (e.g., benzene, toluene, xylene, dimethylformamide, or the like) and further in the presence of a suitable organic base (e.g., trimethylamine, triethylamine, pyridine, or the like), at standard pressure, at a temperature of from room temperature to the boiling point of the solvent employed and for a period of time ranging from approximately 2 to 48 hours. Alternatively, in this reaction, the organic base can serve as the solvent. In the course of the reaction, when the steroidal starting material is a $\Delta^{4}$ compound, the 4(5)-double bond sometimes migrates to the 5(6)-position. Generally, a mixture of $\Delta^{4}$ and $\Delta^{5(6)}$ compounds results. In certain cases, it has been found that use of the reagent of formula (III) in the form of a hydrochloride salt will result in predominantly $\Delta^{5(6)}$ compounds, whereas use of the reagent in the form of the free base yields predominantly $\Delta^{4}$ steroid. However, the nature of the particular reagent of formula (III) and the steroidal starting material employed can also influence the location of the double bond, as can the manner of isolation of the final product. While control of reaction conditions and isolation techniques so as to afford the $\Delta^{4}$ compounds is preferred because the $\Delta^{4}$ compounds on hydrolysis go directly to the parent hormone, the $\Delta^{5(6)}$ derivatives are also highly desirable because they readily undergo hydrolysis and rearrangement of the double bond to the $\Delta^{4}$ parent hormone.

In the case of the compounds of formula (I), the reaction of equal molar quantities of steroid and reagent of formula (III) affords the 3-spiro dirivative, while the use of a large excess (about 6 equivalents) of reagent of formula (III) yields a product having the thiazolidine grouping at both the 3- and 20-positions. The compound of formula (I) wherein the 3-substituent is an oxo group and the grouping at 20 is a thiazolidine is generally present in the reaction mixture as a unisolated intermediate.

The compounds resulting from the process described above correspond to formulae (I) and (II) wherein $R_6$ is hydrogen. Further treatment of those products with a conventional acylating agent (e.g., acetic anhydride or propionic anhydride in pyridine) affords the corresponding compounds wherein $R_6$ is —$COR_7$ or —$COOR_7$.

A desirable alternate route to the compounds of formula (I) wherein the 1,2-linkage is unsaturated begins by reacting acetone with a reagent of formula (III) above. The product, a compound of the formula

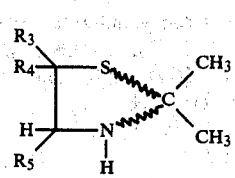

is then heated with a 3,20-diketo steroid, in the presence of an acid catalyst, using a large excess of the depicted thiazolidine reactant, to effect transfer of the thiazolidine grouping to the steroid and provide the desired compound of formula (I).

The starting materials used in the preparation of the compounds of formulae (I) and (II) can be prepared by known methods; thus, for example, the methods set forth in Example (I) below are applicable to the preparation of various compounds of formula (III).

The invention will appear more fully from the examples which follow. These examples are given by way of illustration only and are not to be construed as limiting the invention either in spirit or in scope as many modifications both in materials and in methods will be apparent to those skilled in the art.

EXAMPLE I

ILLUSTRATIVE PREPARATION OF STARTING MATERIALS (a) L-Cysteine butyl ester hydrochloride L-Cysteine hydrochloride (100 g) was dissolved in 250 ml of butanol saturated with dry HCl. The solution was heated under reflux for 4 hours. Excess of solvent was evaporated under evaporator. Ethyl acetate (150 ml) was added to the residue to give crystals. The crystals were recrystallized from ethyl acetate, mp 91° C., yield 30%, IR (KBr) 1745 cm$^{-1}$; NMR (CDCl$_3$) δ9.2–8.4 (b, 3, NH$_3^\oplus$), 4.7 (t, 1, —CH), 4.3 (t, 2-, —CH$_2$)—„ 3.3 (b, 2, CH$_2$S), 1.0 (t, 3, —CH$_3$—), 1.0–3.0 (m, 4, —CH$_2$CH$_2$).

Anal. Calcd for C$_7$H$_{16}$ClNO$_2$S: C, 39.33; H, 7.54; N, 6.55. Found: C, 39.70; H, 7.59; N, 6.50.

(b) L-Cysteine hexyl ester hydrochloride

L-Cysteine hydrochloride (78.5 g) was added to 150 ml of hexanol saturated with dry HCl gas. The mixture was heated under reflux overnight. The solution was evaporated to about half of the total volume, and then ethyl ether (150 ml) was added. The solution gave crystals when it was cooled. The crystals were filtered and were then recyrstallized from ethyl acetate; yield 45 g; mp 89°–90° C.; IR (KBr) 1745 cm$^{-1}$; NMR (CDCl$_3$) δ9.2–8.4 (b, 3, NH$_3^\oplus$), 4.7 (t, 1, —CH—), 4.3 (t, 2, —OCH$_2$—), 3.4 (b, 2, CH$_2$S—), 1.0–3.0 (m, 8), 1.0 (t, 3-, CH$_3$).

(c) L-Cysteine decyl ester hydrochloride

L-Cysteine (157.4 g) was added to 250 ml of decyl alcohol saturated with dry HCl. The mixture was heated to 150° C. for 6 hours. The solution was cooled and was mixed with an equal volume of ethyl acetate. The solution was cooled in a dry ice bath to give crystals. The crystals were filtered and were then recrystallized from ethyl acetate, mp 96°–99° C., yield 100 g, IR (KBr) 1745 cm$^{-1}$.

EXAMPLE II

Preparation of 17β-(4''-Butyloxycarbonyl-2''-methyl-1'',3''-thiazolidin-2''-yl)-4-androstene-3-spiro-2'-(4'-butyloxycarbonyl-1',3'-thiazolidine) and the corresponding Δ$^{5(6)}$ compound:

Progesterone (6.3 g, 0.02 mole) was dissolved in 50 ml of pyridine to which was added 20 g (0.094 mole) of L-cysteine butyl ester hydrochloride. After purging the system with nitrogen for 0.25 hour, the reaction mixture was stirred overnight at room temperature. Excess of pyridine was evaporated. The residue was dissolved in 150 ml. of methylene chloride and the solution was washed twice with 100 ml portions of water. The separated methylene chloride solution was dried over MgSO$_4$. After methylene chloride was evaporated, the residue was boiled with 150 ml of methanol. The crystals were filtered while the methanol solution was hot. The crystals were further recrystallized from ethanol to give the desired product; mp 149°–150° C., 2 g, IR (KBr) 1745 cm$^{-1}$ (s) (C═O); NMR (CDCl$_3$) δ5.55–5.25 (m, 1, CH═C), 4.45–3.7 (m, 6, CH$_2$O, CH$_2$S), 3.7–2.3 (m, 6, CH$_2$S, CHN, and NH), 1.57 (s, 3, CH$_3$—C(—S)—N), 1.03 (s, 3, CH$_3$C), 0.85 (s, 3, CH$_3$C) and 2.3–0.7 (m, 32, CH$_2$CH$_3$).

Anal. Calcd for C$_{35}$H$_{56}$N$_2$S$_2$O$_4$: C, 66.42; H, 8.92; N, 4.43. Found: C, 66.90; H, 9.20; N, 4.30.

EXAMPLE III

Preparation of 17β-(4''-hexyloxycarbonyl-2''-methyl-1'',3''-thiazolidin-2''-yl)-4-androstene-3-spiro-2'-(4'-hexyloxycarbonyl-1',3'-thiazolidine) and the corresponding Δ$^{5(6)}$ compound:

Progesterone (6.3 g, 0.02 mole) was dissolved in 50 ml of pyridine to which was added 20 g (0.080 mole) of L-cysteine hexyl ester hydrochloride. After purging the system with nitrogen for 0.25 hour, the reaction mixture was stirred overnight at room temperature. The solution was mixed with 200 ml of ether. The ether solution was washed with 200 ml of water. The water solution was extracted with another 150 ml of ether. The combined ether solutions were dried with MgSO$_4$. After the ether was evaporated, the residue was treated with 100 ml of methanol to give crystals after standing overnight. The crystals were recrystallized from ethanol to give 4 g of desired product, mp 113°–115° C.; IR (KBr) 1745 cm$^{-1}$ (s) (C═O); NMR (CDCl$_3$) δ5.55–5.25 (m, 1, CH═C), 4.45–3.7 (m, CH$_2$O, CH$_2$S), 3.7–2.3 (m, 6, CH$_2$S,CHN, and NH), 1.57 (s, 3, CH$_3$—C(—S)—N), 1.03 (s, 3, CH$_3$C), 0.85 (s, 3, CH$_3$C) and 2.3–0.7 (m, 40, CH$_2$).

Anal. Calcd for C$_9$H$_{64}$O$_4$S$_2$N$_2$: C, 67.98; H, 9.36; N, 4.07. Found: C, 68.40; H, 9.48; N, 3.90.

EXAMPLE IV

Preparation of 17β-(4''-Decyloxycarbonyl-2''-methyl-1'',3''-thiazolidin-2''-yl)-4-androstene-3-spiro-2'-(4'-decyloxycarbonyl-1',3'-thiazolidine) and the corresponding Δ$^{5(6)}$ compound:

Progesterone (6.3 g, 0.02 mole) was dissolved in 80 ml of pyridine to which was added 22 g (0.072 mole) of L-cysteine decyl ester hydrochloride. After purging the system with nitrogen for 0.25 hour, the reaction mixture was stirred overnight at room temperature. Excess of pyridine was evaporated. The residue was dissolved in 150 ml of $CH_2Cl_2$ and the solution was washed with 500 ml of water. The organic layer was dried with $MgSO_4$. After the $CH_2Cl_2$ was evaporated, ethanol (100 ml) was added to give crystals. The crystals were recrystallized from ethanol, mp. 100°–102° C.; IR (KBr) 1745 cm$^{-1}$; NMR (CDCl$_3$) δ5.55–5.25 (m, 1, CH=C); 4.45–3.7 (m, 6, CH$_2$O, CH$_2$S), 3.7–2.3 (m, 6, CH$_2$S, CHN and NH), 1.57 (s, 3, CH$_3$—C(S)—N), 1.03 (s, 3, CH$_3$C), 0.85 (s, 3, CH$_3$C) and 2.3–0.7 (m, 56, CH$_2$, CH$_3$).

Anal. Calcd for $C_{47}H_{80}N_2S_2O_4$: C, 70.45; H, 10.06; N, 3.50. Found: C, 70.62; H, 10.20; N, 3.40.

EXAMPLE V

Preparation of 17β-Propionyloxy-4-and 17β-propionyloxy-5-androstene-3-spiro-2'-(4'-ethoxycarbonyl-1',3'-thiazolidine):

To a mixture of testosterone17-propionate (1.0 g, 0.0029 mole) and cysteine ethyl ester hydrochloride (3.70 g, 0.02 mole) was added 10 ml of pyridine. The solution was allowed to sit at room temperature overnight under a nitrogen atmosphere in a tightly closed flask. The solution was then processed as described above to give a solid residue which was crystallized from 10 ml of hot ethanol to give 0.35 g (mp 144°–147° C., 26% yield) of 17β-propionyloxy-5-androstene-3-spiro-2'-(4'-ethoxycarbonyl-1',3'-thiazolidine): TLC (silica gel, ether) Rf 0.45; IR (KBr) 1735 cm$^{-1}$ (s) (C=O); $^1$H NMR (CDCl$_3$) δ5.53–5.2 (m, 1, CH=C), 4.6 (t, J=8 Hz, 1, CHO$_2$C), 4.21 (q, J=7 Hz, 2, CH$_3$CH$_2$O, 4.2–3.8 (m, 1, O$_2$CCHN), 3.4–2.7 (m, 2, CH$_2$S), 1.29 (t, J=7 Hz, 3, CH$_3$CH$_2$O), 1.01 (s, 3, CH$_3$—C), 0.8 (s, 3, CH$_3$—C), 2.7–1.0 (m, 24, CH$_3$, CH$_2$ and CH); $^{13}$c NMR (CDCl$_3$) δ174.7, 171.9 (CO$_2$), 140.7 (C$_5$) and 122.4 (C$_6$); [α]$^{27}$ D–54.9° (C=0.55, ethanol).

Anal. Calcd for $C_{27}H_{41}NO_4S$: C, 68.17; H, 8.69; N, 2.95. Found: C, 68.46; H, 8.78; N, 2.70.

The mother liquor was concentrated to 5 ml and allowed to crystallize further. There was obtained 0.51 g (mp 100°–104° C., 37% yield) of a mixture containing 17β-propionyloxy-4-and 17β-propionyloxy-5-androstene-3-spiro-2'-(4'-ethoxycarbonyl-1',3'-thiazolidine), in the ratio of 8:2. TLC and IR the same as above: $^1$H NMR also the same except the main CH=C absorption is a singlet at δ5.3; $^{13}$C NMR (CDCl$_3$) 174.7, 171.9 (CO$_2$), 148.6 (C$_5$) and 123 (C$_4$); [α]$^{27}$ D+9.9 (C=0.49, ethanol).

Anal. Calcd for $C_{27}H_{41}NO_4S$: C, 68.17; H, 8.69; N, 2.95 Found: C, 68.28; H, 8.79; N, 2.75.

EXAMPLE VI

Preparation of 17β-(4''-Methoxycarbonyl-2''-methyl-1'',3''-thiazolidin-2''-yl)-4-androstene-3-spiro-2'-(4'-methoxycarbonyl-1',3'-thiazolidine):

Cysteine methyl ester hydrochloride (9.5 g, 0.06 mole) was suspended in 60 ml triethylamine and allowed to react under reflux for one hour. Cooling to room temperature, followed by filtration of the solid material, gave a quantitative yield of triethylamine hydrochloride. The excess triethylamine in the filtrate was evaporated leaving cysteine methyl ester as an oil. The purity of the ester was determined by nmr. The ester was added to a 15 ml pyridine solution of progesterone (3.2 g, 0.01 mol) at room temperature and allowed to react for 2 days. The desired product precipitated from the reaction mixture as it was formed. Filtration of the solid followed by recrystallization from ethanol gave 2.0 g (0.036 mol, 36%), of the desired product, mp 168°–169° C., IR (KBr) 2940 and 1760 cm$^{-1}$; nmr (CDCl$_3$) δ5.3 (s, 1H, CH=C), 3.8 (s, 6H, —CO$_2$CH$_3$) 1.6 (s, 3H, 21-C), 1.0 (s, 3H, 18-C), 0.8 (s, 3H, 19-C), and 4.3–0.7 (m, 28H); [α]$^{25.10}$D= –12.0° (C=1.08, CHCl$_3$).

Anal. Calcd for $C_{29}H_{44}N_2O_4S_2$: C, 63.47; H, 8.08; N, 5.11. Found: C, 63.49; H, 8.15; N, 5.21.

Evaporation of the filtrate gave an oil which crystallized from methanol to give 0.8 g (0.0015 mol, 15%) as a mixture of the desired product (67%) and the corresponding Δ$^{5(6)}$ compound (33%).

EXAMPLE VII

Preparation of 5-Androstene-3-spiro-2'-(4'-ethoxycarbonyl-1',3'-thiazolidine)-17β-ol To a 25 ml pyridine solution of cysteine ethyl ester hydrochloride (7.4 g, 0.04 mol) was added testosterone (5.8 g, 0.02 mol) at room temperature. The resulting solution was allowed to react overnight. Evaporation of the pyridine gave the product as an oil. Crystallization from ethanol gave a mixture of the desired product and its Δ$^4$ isomer. Recrystallization of this product from methanol gave 1.3 g (0.003 mol, 15%) of the desired product; mp 152°–155° C., IR (KBr) 3300, 2940, and 1740 cm$^{-1}$; nmr (CDCl$_3$) δ5.4 (m, 1H, CH=C), 4.2 (q, 2H, CO$_2$CH$_2$CH$_3$), 4.0–2.7 (m, 5H), 2.4–0.7 (m, 23H) 1.0 (s, 3H) and 0.7 (s, 3H); [α]$^{26.3°}$ D= –95.9° (C=0.98, CHCl$_3$).

Addition of water to the methanol filtrate yielded 1.7 g (0.004 mol, 21%) mixture of the desired product (70%) and 4- androstene-3-spiro2'-(4'-ethoxycarbonyl-1',3'-thiazolidine)-17β-ol (30%).

EXAMPLE VIII

Preparation of 4-Pregnene-3-Spiro-2'-(4'-ethoxycarbonyl-1',3'-thiazolidine)-20-one 17β-(4''-Ethoxycarbonyl-2''-methyl-1'',-3''-thiazolidin-2''-yl)-5-androstene-3-spiro-2'-(4'-ethoxycarbonyl-1',3'-thiazolidine) (1.0 g) was heated in 25 ml of 80% acetic acid at 65° C. for 3.5 minutes, then quickly neutralized with 400 ml of ice cold water containing 25 g of NaHCO$_3$. The suspension that resulted was filtered and dried to give 0.41 g of a white solid which was about 65% pure. The solid was crystallized from ethanol (7 ml) to give 0.22 g (mp 127°–134° C., 28% yield) of the desired product: IR(KBr) 1735 and 1700 cm$^{-1}$ (s) (C=O); $^1$H NMR (CDCl$_3$) δ5.30 (s, 1, CH=C), 4.23 (q, J=7 Hz, 2, CH$_3$CH$_2$O), 4.4–3.9 (m, 1, O$_2$CCHN), 3.6–2.8 (m, 2, CH$_2$S), 2.15 (s, 3, CH$_3$—C=O), 1.3 (t, 3, J=7 Hz, CH$_3$CH$_2$O), 1.03 (s, 3, CH$_3$—C$_{10}$), 0.63 (s, 3, CH$_3$—C$_{13}$), 2.8–0.6 (m, 19, CH$_2$ and CH); $^{13}$C NMR (CDCl$_3$) δ209.71 (C$_{20}$=O), 171.87 (CO$_2$), 148.7 (C$_5$) and 123.06 (C$_6$); [α]$^{25}$D+98.2 (C=0.47, CHCl$_3$).

Anal. Calcd for $C_{26}H_{39}NO_3S$: C, 70.07; H, 8.82; N, 3.14. Found: C, 70.00; H, 8.89; N, 2.55.

EXAMPLE IX

Preparation of 17β-(4'''-Ethoxycarbonyl-2''-methyl-1'',3''-thiazolidin-2''-yl)-4-androstene-3-spiro-2'-(4'-ethoxycarbonyl-1',3'-thiazolidine):

Cysteine ethyl ester hydrochloride (11.2 g, 0.06 mole) was suspended in 40 ml of triethylamine with vigorous stirring for one hour at room temperature. The triethylamine hydrochloride was filtered and filtrate was concentrated to give cysteine ethyl ester as an oil. The oil was dissolved in 30 ml of pyridine and allowed to react with 3.2 g (0.01 mole) of progesterone at room temperature for 3.5 days. The suspension that resulted was filtered and crystallized from ethyl acetate to give 2.7 g (mp 162°–165° C., 47% yield) of the desired product: IR(KBr) 1740 cm$^{-1}$(s) (C=O); $^1$H NMR (CDCl$_3$) δ5.23 (s, 1, CH=C), 4.2 (q, J=7 Hz, 4, CH$_3$CH$_2$O), 4.2–3.6 (m, 2, O$_2$CCHN), 3.50–2.65 (m, 4, CH$_2$S), 1.55 (s, 3, CH$_3$—C$_{20}$), 1.3 (t, J=7 Hz, 6, CH$_3$CH$_2$O), 1.03 (s, 3, CH$_3$—C$_{10}$), 0.85 (s, 3, CH$_3$—C$_{13}$), 2.6–0.6 (m, 19, CH$_2$ and CH); $^{13}$C NMR (CDCl$_3$) δ171.88 and 171.99 (CO$_2$), 148.86 (C$_5$) and 122.89 (C$_4$); [α]$^{24.5}$D −24.3° (C=0.63, CHCl$_3$).

Anal. Calcd for C$_{31}$H$_{48}$N$_2$O$_4$S$_2$: C, 64.54; H, 8.39; N, 4.86. Found: C, 64.59; H, 8.46; N, 4.88.

EXAMPLE X

Reaction of Progesterone with Cysteine Ethyl Ester Hydrochloride

Progesterone (1.0 g, 0.0032 mole) was mixed with increasing amounts of cysteine ethyl ester hydrochloride (0.65 g, 0.0035 mole, one equivalent; 1.30 g, 0.0070 mole, two equivalents; 2.60 g, 0.014 mole, four equivalents; 3.90 g, 0.021 mole, six equivalents) and dissolved in pyridine (10 ml) in four separate reactions. The reaction mixtures were then kept at room temperature overnight under a nitrogen atmosphere in a tightly closed flask. Each reaction mixture was then concentrated in vacuo (0.1 mm, 1 hour, 45° C.) to give a gummy solid which was suspended in 50 ml of CH$_2$Cl$_2$. The CH$_2$Cl$_2$ suspensions were extracted with 10 ml of water, dried over Na$_2$SO$_4$ and concentrated in vacuo to give yellow solids which were analyzed by TLC and NMR spectroscopy. Only the reaction with six equivalents of cysteine ethyl ester hydrochloride appeared to give a homogenous product. All of the reaction products were suspended in 25 ml of boiling ethanol and filtered. In the case of the reactions with four and six equivalents, there was considerable amount of the ethanol insoluble material. The ethanol insoluble fraction from the reaction with four equivalents of cysteine ethyl ester hydrochloride was a mixture but that from six equivalents was homogenous and it was identified as 17β-(4″-ethoxycarbonyl-2″-methyl-1″,3″-thiazolidin-2″-yl)-5-androstene-3-spiro-2′-(4′-ethoxycarbonyl-1′,3′-thiazolidine): 1.2 g; mp 167°–170° C.; 67% yield; IR (KBr) 1735 cm$^{-1}$ (s) (C=O); $^1$H NMR (CDCl$_3$) δ5.6–5.2 (m, 1, CH=C), 4.20 (q, J=7 Hz, 4, OCH$_2$CH$_3$), 4.1–3.65 (m, 2, O$_2$C-CH—N), 3.5–2.6 (m, 4, CH$_2$—S), 1.57 (s, 3, CH$_3$—C$_{20}$), 1.03 (s, 3, CH$_3$—C$_{10}$), 0.85 (s, 3, CH$_3$—C$_{13}$), 1.3 (t, J=7 Hz, 6, CH$_3$CH$_2$O), 2.6–0.6 (m, 19, CH$_2$ and CH); $^{13}$C NMR (CDCl$_3$) δ171.933 (CO$_2$), 140,606 (C$_5$) and 122.503 (C$_4$); [α]$^{27}$D −81° (C=0.56, CHCl$_3$); TLC (silica gel, ether) Rf 0.42.

Anal. Calcd for C$_{31}$H$_{48}$N$_2$O$_4$S$_2$: C, 64.54; H, 8.39; N, 4.86; Found: C, 64.61; H, 8.44; N, 4.63. Crystallization of that product from ethanol or ethyl acetate resulted in mixtures containing up to 30% of the 4-pregnene isomer.

The crystals obtained from the 25 ml ethanol solutions above contained mixtures except for the product from the reaction with one equivalent of cysteine ethyl ester hydrochloride. Those crystals were identified as a 4:1 mixture of 5- and 4-pregnene-3-spiro-2′-(4′-ethoxycarbonyl-1′,3′-thiazolidine)-20-one: 0.45 g; mp 127°–134° C.; 33% yield; IR(KBr) 1735 and 1700 cm$^{-1}$ (s) (C=O); $^1$H NMR (CDCl$_3$) δ5.6–5.2 (m, 1, CH=C), 4.26 (q, J=7 Hz, 2, CH$_3$CH$_2$O), 4.2–3.8 (m, 1, O$_2$CCHN), 3.6–2.8 (m, 2, CH$_2$S), 2.11 (S, 3, CH$_3$—C$_{20}$), 1.03 (s, 3, CH$_3$—C$_{10}$), 0.63 (s, 3, CH$_3$—C$_{13}$), 1.3 (t, J=7 Hz, 3, CH$_3$CH$_2$O), 2.8–0.6 (m, 19, CH$_2$ and CH); $^{13}$C NMR (CDCl$_3$) δ209.676 (C$_{20}$=O), 171.922 (CO$_2$), 140.559 (C$_5$) and 122.460 (C$_6$); [α]$^{27}$D +11.2° (C=0.58, CHCl$_3$); TLC (silica gel, ether) Rf 0.34.

Anal Calcd for C$_{26}$H$_{39}$NO$_3$S: C, 70.07; H, 8.82; N, 3.14. Found: C, 69.84; H, 8.80; N, 3.05.

In the case where six equivalents of cysteine ethyl ester hydrochloride was used, after the reaction was allowed to run overnight, a precipitate formed. That precipitate could be filtered to give (mp 164°–170° C., [α]$^{e°}$ D −92.1 (C=0.66, CHCL$_3$), 61% of 17β-(4″-ethoxycarbonyl-2″-methyl-1″,3″-thiazolidin-2″-yl)-5-androstene-3-spiro-2′-(4′-ethoxycarbonyl-1′,3′-thiazolidine) and an additional 18% could be obtained upon processing the filtrate, which was a 50:50 mixture of 17β-(4″-ethoxycarbonyl-2″-methyl-1″,3″-thiazolidin-2″-yl)-4-androstene-3-spiro-2′-(4′-ethoxycarbonyl-1′,3′-thiazolidine) and the corresponding Δ$^{5(6)}$ compound.

EXAMPLE XI

Following those procedures and methods outlined in the foregoing Examples, but substituting the appropriate generally and/or specifically described reactants and/or operating conditions, the following additional compounds according to the invention are prepared:

17β-(4″-tert-Butyloxycarbonyl-2″-methyl-1″,3″-thiazolidin-2″-yl)-4-androstene-3-spiro-2′-(4′-tert-butyloxycarbonyl-1′,3′-thiazolidine) and the corresponding Δ$^{5(6)}$ compound;

17β-(4″-Benzyloxycarbonyl-2″-methyl-1″,3″-thiazolidin-2″-yl)-4-androstene-3-spiro-2′-(4′-benzyloxycarbonyl-1′,3′-thiazolidine) and the corresponding Δ$^{5(6)}$ compound;

17β-(4″-Isopropyloxycarbonyl-2″-methyl-1″,3″-thiazolidin-2″-yl)-4-androstene-3-spiro-2′-(4′-isopropyloxycarbonyl-1′,3′-thiazolidine) and the corresponding Δ$^{5(6)}$ compound; 4- and 5-Pregnene-3-spiro-2′-(4′-ethoxycarbonyl-1′,3′-thiazolidine)-20-one;

4- and 5-Pregnene-3-spiro-2′-(4′-butyloxycarbonyl-1′,3′-thiazolidine)-20-one;

4- and 5-Pregnene-3-spiro-2′-(4′-hexyloxycarbonyl-1′,3′-thiazolidine)-20-one;

4- and 5-Pregnene-3-spiro-2′-(4′-decyloxycarbonyl-1′,3′-thiazolidine)-20-one;

4- and 5-Pregnene-3-spiro-2′-(4′-tert-butyloxycarbonyl-1′,3′,-thiazolidine)-20-one;

4- and 5-Pregnene-3-spiro-2′-(4′-benzyloxycarbonyl-1′,3′-thiazolidine)-20-one;

4- and 5-Pregnene-3-spiro-2′-(4-isopropyloxycarbonyl-1′,3′-thiazolidine)-20-one;

17β-(4″-Ethoxycarbonyl-2″,5″,5″-trimethyl-1″,3″-thiazolidin-2″-yl)-4-androstene-3-spiro-2′-(4′-ethoxycarbonyl-5′,5′-dimethyl-1′,3′-thiazolidine) and the corresponding Δ$^{5(6)}$ compound;

17β-(4″-Hexyloxycarbonyl-2″,5″,5″-trimethyl-1″,3″-thiazolidin-2″-yl)-4-androstene-3-spiro-2′-(4′-hexyloxycarbonyl-5′,5′-dimethyl-1′,3′-thiazolidine) and the corresponding Δ$^{5(6)}$ compound;

17β-(4″-Butyloxycarbonyl-2″,5″,5″-trimethyl-1″,3″-thiazolidin-2″-yl)-4-androstene-3-spiro-2′-(4′-butyloxycarbonyl-5′,5′-dimethyl-1′,3′-thiazolidine) and the corresponding Δ$^{5(6)}$ compound;

6α-Chloro-17β-(4'''-ethoxycarbonyl-2'''-methyl-1''',3'''-thiazolidin-2'''-yl)-4-androstene-3-spiro-2'-(4'-ethoxycarbonyl-1',3'-thiazolidine) and the corresponding $\Delta^{5(6)}$ compound;

17β-(4'''-Butyloxycarbonyl-2'''-methyl-1''',3'''-thiazolidin-2'''-yl)-6α-chloro-4-androstene-3-spiro-2'-(4'-butyloxycarbonyl-1',3'-thiazolidine) and the corresponding $\Delta^{5(6)}$ compound;

6α-Chloro-17β-(4'''-hexyloxycarbonyl-2'''-methyl-1''',3'''-thiazolidin-2'''-yl)-4-androstene-3-spiro-2'-(4'-hexyloxycarbonyl-1',3',-thiazolidine) and the corresponding $\Delta^{5(6)}$ compound;

17α-Acetyloxy-17β-(4'''-ethoxycarbonyl-2'''-methyl-1''',3'''-thiazolidin-2'''-yl)-6α-methyl-4-androstene-3-spiro-2'-(4'-ethoxycarbonyl-1',3'-thiazolidine) and the corresponding $\Delta^{5(6)}$ compound;

17α-Acetyloxy-17β-(4'''-butyloxycarbonyl-2'''-methyl-1''',3'''-thiazolidin-2'''-yl)-6α-methyl-4-androstene-3-spiro-2'-(4'-butyloxycarbonyl-1',3'-thiazolidine) and the corresponding $\Delta^{5(6)}$ compound;

17α-Acetyloxy-17β-(4'''-hexyloxycarbonyl-2'''-methyl-1''',3'''-thiazolidin-2'''-yl)-6α-methyl-4-androstene-3-spiro-2'-(4'-hexyloxycarbonyl-1',3'-thiazolidine) and the corresponding $\Delta^{5(6)}$ compound;

17α-Acetyloxy-17β-(4'''-ethoxycarbonyl-2'''-methyl-1''',3'''-thiazolidin-2'''-yl)-9α-fluoro-4-androstene-3-spiro-2'-(4'-ethoxycarbonyl-1',3'-thiazolidine) and the corresponding $\Delta^{5(6)}$ compound;

17α-Acetyloxy-17β-(4'''-butyloxycarbonyl-2'''-methyl-1''',3'''-thiazolidin-2'''-yl)-9α-fluoro-4-androstene-3-spiro-2'-(4'-butyloxycarbonyl-1',3'-thiazolidine) and the corresponding $\Delta^{5(6)}$ compound;

17α-Acetyloxy-9α-fluoro-17β-(4'''-hexyloxycarbonyl-2'''-methyl-1''',3'''-thiazolidin-2'''-yl)-4-androstene-3-spiro-2'-(4'-hexyloxycarbonyl-1',3'-thiazolidine) and the corresponding $\Delta^{5(6)}$ compound;

17α-Acetyloxy-6α-methyl-4-pregnene-3-spiro-2'-(4'-ethoxycarbonyl-1',3'-thiazolidine)-20-one and the corresponding $\Delta^{5(6)}$ compound;

17α-Acetyloxy-6α-methyl-4-pregnene-3-spiro-2'-(4'-hexyloxycarbonyl-1',3'-thiazolidine)-20-one and the corresponding $\Delta^{5(6)}$ compound;

17α-Acetyloxy-6α-methyl-4-pregnene-3-spiro-2'-(4'-isopropyloxycarbonyl-1',3'-thiazolidine)-20-one and the corresponding $\Delta^{5(6)}$ compound;

17β-[3'',4''-di(Ethoxycarbonyl)-2''-methyl-1'',3''-thiazolidin-2''-yl]-4-androstene-3-spiro-2'-[3',4'-di(ethoxycarbonyl)-1',3'-thiazolidine] and the corresponding $\Delta^{5(6)}$ compound;

17β-(4'''-Carboxy-2''',5''',5'''-trimethyl-1''',3'''-thiazolidin-2'''-yl)-4-androstene-3-spiro-2'-(4'-carboxy-5',5'-dimethyl-1',3'-thiazolidine) and the corresponding $\Delta^{5(6)}$ compound;

17α-Ethynyl-4-and 17α-ethynyl-5-androstene-3-spiro-2'-(4'-ethoxycarbonyl-1',3'-thiazolidine)-17β-ol;

17α-Ethynyl-19-nor-4-and 17α-ethynyl-19-nor-5-addrostene-3-spiro-2'-(4'-ethoxycarbonyl-1',3'-thiazolidine)-17β-ol;

4-and 5-Androstene-3-spiro-2'-(4'-carboxy-1',3'-thiazolidine)-17β-ol;

4- and 5-Androstene-3-spiro-2'-(4'-ethoxycarbonyl-1',3'-thiazolidine)-17β-ol;

4- and 5-Androstene-3-spiro-2'-(4'-hexyloxycarbonyl-1',3'-thiazolidine)-17β-ol;

4- and 5-Androstene-3-spiro-2'-(4'-butyloxycarbonyl-5',5'-dimethyl-1',3'-thiazolidine)-17β-ol;

4- and 5-Androstene-3-spiro-2'-(4'-ethoxycarbonyl-1',3'-thiazolidine)-17β-ol 17-propionate;

19-Nor-4-and 19-nor-5-androstene-3-spiro-2'-(4'-ethoxycarbonyl-1',3'-thiazolidine)-17β-ol 17-propionate;

19-Nor-4-and 19-nor-5-androstene-3-spiro-2'-(4'-ethoxycarbonyl-1',3'-thiazolidine)-17β-ol 17-adamantyl carboxylate;

19-Nor-4-and 19-nor-5-androstene-3-spiro-2'-(4'-ethoxycarbonyl-1',3'-thiazolidine)-17β-ol 17-phenylpropionate;

4- and 5-Androstene-3-spiro-2'-(4'-ethoxycarbonyl-5',5'-dimethyl-1',3'-thiazolidine) 17β-ol.

EXAMPLE XII

Preparation of 17β-Propionyloxy-5-androstene-3-spiro-2'-(1',3'-thiazolidine):

To 1.0 g (0.0028 mole) of testosterone 17β-propionate dissolved in 10 ml of pyridine was added 1.7 g (0.015 mole) of 2-aminoethanethiol hydrochloride. The suspension was stirred at room temperature under a nitrogen atmosphere for 24 hours. The solvent was then evaporated and the yellow-orange residue that remained was triturated with $CH_2Cl_2$ (100 ml). The suspension that resulted was filtered to remove residual 2-aminoethanethiol hydrochloride. The filtrate was extracted with 100 ml of water. The $CH_2Cl_2$ layer was separated, dried over $Na_2SO_4$ and concentrated in vacuo to give 0.95 (mp 136°–148° C., 89% yield) of the desired product based on its NMR spectrum. The solid was crystallized from methanol to give 0.75 g (mp 152°–157° C.) of pure product. TLC (silica gel, ether) Rf 0.16; IR (KBr) 1730 cm$^{-1}$ (S) (C=O); 1H NMR (CDCl$_3$) δ5.5–5.3 (m, 1, 0=C—C$\underline{H}$=C), 4.63 (t, 1, J=8 Hz, C$\underline{H}$—O$_2$C), 3.6–2.8 (m, 4 S—C$\underline{H_2CH_2}$N), 1.07 (s, 3, C$\underline{H_3}$—C), 0.83 (s, 3, C$\underline{H_3}$—C), 1.17 (t, 3, J=7 Hz, O$_2$CCH$_2$C$\underline{H_3}$), 2.8–0.7 (m, 22, C$\underline{H_2}$, C$\underline{H}$ and N$\underline{H}$); $[\alpha]^{23}D+69.0$ (C=0.52, CHCl$_3$).

Anal. Calcd for $C_{24}H_{37}NO_2S$: C, 71.41; H, 9.24; N, 3.47. Found: C, 71.32; H, 9.38, N, 3.15.

EXAMPLE XIII

Preparation of 5-Pregnene-3-spiro-2'-(1',3'-thiazolidine)-20-one:

A mixture of 3.14 g (0.01 mole) of progesterone and 6.7 g (0.06 mole) of 2-aminoethanethiol was suspended in 20 ml of pyridine overnight at room temperature under a nitrogen atmosphere. The suspension was concentrated in vacuo. The residue that resulted was partitioned between $CH_2Cl_2$ and $H_2O$ (100:150, ml). The $CH_2Cl_2$ layer was dried over $Na_2SO_4$ and concentrated. The residue from the $CH_2Cl_2$ layer was triturated with 10 ml of warm methanol; almost all of the residue went into solution. After the suspension had cooled, it was filtered to give 1.72 g (mp 127°–136° C., 46% yield) of the desired compound: TLC (silica gel, ether) Rf 0.20; IR (KBr) 3300 cm$^{-1}$ (w) (N-H), 1700 cm$^{-1}$ (s)(C=O); NMR (CDCl$_3$) 5.31 (m, 1, C$\underline{H}$=C), 3.6–2.9 (m, 4, SC$\underline{H_2}$—C$\underline{H_2}$—N), 2.11 (s, 3, C$\underline{H_3}$C=O), 1.03 (s, 3, C$\underline{H_3}$—C), 0.63 (s, 3, C$\underline{H_3}$—C) and 2.9–0.6 (m, 21, C$\underline{H_2}$, C$\underline{H}$ and N$\underline{H}$); $[\alpha]$ D+104 (C=0.51, CHCl$_3$).

Anal. Calcd. for $C_{23}H_{35}NOS$: C, 73.94; H, 9.44; N, 3.75. Found: C, 73.69; H, 9.80; N, 4.00.

The compounds of the present invention are conveniently administered to warm-blooded animals via conventional oral administration with any suitable nontoxic pharmaceutically acceptable oral inert carrier material. Such carrier materals are well-known to those skilled in the art of oral pharmaceutical formulations. For those not skilled in the art, reference is made to the text entitled REMINGTON'S PHARMACEUTICAL SCIENCES, (Fourteenth Edition), 1970. In a typical preparation for oral administration, e.g., tablet or capsule, any one of the compounds of the instant invention is combined in a progestinically or androgenically effective amount, e.g., a contraceptively effective amount, with any oral nontoxic pharmaceutically acceptable inert carrier such as lactose, starch (pharmaceutical grade), dicalcium phosphate, calcium sulfate, kaolin, mannitol and powdered sugar. Additionally, when required, suitable binders, lubricants, disintegrating agents and coloring agents can also be included. Typical binders include starch, gelatin, sugars such as sucrose, molasses and lactose, natural and synthetic gums such as acacia, sodium alginate, extract of Irish moss, carboxymethylcellulose, methylcellulose, polyvinylpyrrolidone, polyethylene glycol, ethylcellulose and waxes. Typical lubricants for use in these dosage forms can include, without limitation, boric acid, sodium benzoate, sodium acetate, sodium chloride, leucine and polyethylene glycol. Suitable disintegrators can include, without limitation, starch, methylcellulose, agar, bentonite, cellulose, wood products, alginic acid, guar gum, citrus pulp, carboxymethylcellulose and sodium lauryl sulfate. If desired, a conventional pharmaceutically acceptable dye can be incorporated into the dosage unit form, i.e., any of the standard FD&C dyes.

Naturally, the therapeutic dosage range for the compounds of the instant invention will vary with the size and needs of the patient. However, generally speaking, the following dosage guidelines will suffice. On an oral basis, the therapeutic dose required for a compound of the instant invention will generally, on a molecular basis, mimic that for the parent conventional steroid moiety (e.g., progesterone, testosterone, etc.) to elicit its known androgenic or progestinic response, e.g., an antiovulatory response, or the control of fertility in a fertile female mammal. Typically, a daily dose of from about 0.1 to 5 milligrams will suffice, with a usually preferred amount being about 1 milligram/day.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A compound selected from the group consisting of compounds having the structural formulae:

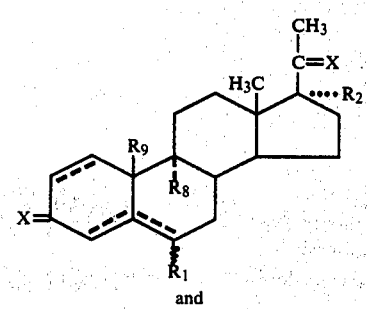

and

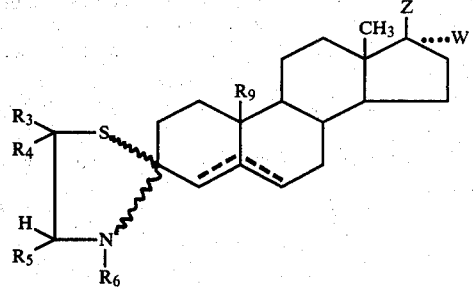

wherein each $=X$ is $=O$ or

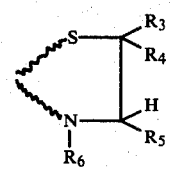

with the proviso that both $=X$'s cannot at the same time be $=O$, albeit either one or both can comprise the depicted thiazolidine nucleus;

$R_1$ is H, $C_1-C_8$ alkyl or halogen;
$R_2$ is H, OH, halogen, $C_1-C_{10}$ alkyl or $-OCOR_7$ wherein $R_7$ is defined as below;
$R_3$ is H or $C_1-C_8$ alkyl;
$R_4$ is H or $C_1-C_8$ alkyl;
$R_5$ is H or $-COOR_7$ wherein $R_7$ is defined as below;
$R_6$ is H, $-COR_7$ or $-COOR_7$, with the proviso that, when $R_6$ is H, then the compound of formula (I) or (II) can also be in the form of a pharmaceutically acceptable acid addition salt;
$R_7$ is H, $C_1-C_{20}$ alkyl, $C_2-C_{20}$ alkenyl, $C_5-C_7$ cycloalkyl, $C_5-C_7$ cycloalkyl-$C_6-C_{10}$ aryl, phenyl or $C_1-C_4$ alkyl-phenyl;
$R_8$ is H, Cl or F;
$R_9$ is H or $C_1-C_8$ alkyl;
$R_{10}$ is H, $C_1-C_8$ alkyl, $C_2-C_8$ alkenyl, $CCl_3$, $CBr_3$, phenyl, $C_6H_5-CH=CH-$ or substituted phenyl wherein the phenyl substituents are selected from the group consisting of lower alkyl, halo and lower alkoxy;
$R_{11}$ is H or $COR_7$ wherein $R_7$ is defined as above;
Z is OH, $OCOR_7$ or

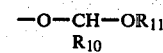

wherein $R_7$, $R_{10}$ and $R_{11}$ are defined as above;
W is H, $C_1-C_{12}$ alkyl, $C_2-C_8$ alkenyl or $C_2-C_8$ alkynyl;
the dotted line at the 1(2)-position in formula (I) indicates the presence of a single or a double bond; and the dotted lines at the 4(5)- and 5(6)-positions indicate the presence of a double bond at either the 4(5)- or the 5(6)-position.

2. A compound as defined by claim 1, having the structural formula (I).

3. A compound as defined by claim 2, wherein the $=X$ at the 3-position comprises the thiazolidine moiety and the $=X$ at the 20-position is $=O$.

4. A compound as defined by claim 2, wherein the =X at the 20-position comprises the thiazolidine moiety and the =X at the 3-position is =O.

5. A compound as defined by claim 2, wherein each =X comprises a thiazolidine moiety.

6. A compound as defined by claim 2, wherein $R_1$ is hydrogen.

7. A compound as defined by claim 2, wherein $R_1$ is $C_1-C_8$ alkyl.

8. A compound as defined by claim 2, wherein $R_1$ is halogen.

9. A compound as defined by claim 2, wherein $R_2$ is hydroxy.

10. A compound as defined by claim 2, wherein $R_2$ is hydrogen.

11. A compound as defined by claim 2, wherein $R_2$ is $-OCOR_7$.

12. A compound as defined by claim 2, wherein $R_2$ is halogen.

13. A compound as defined by claim 2, wherein $R_2$ is $C_1-C_{10}$ alkyl.

14. A compound as defined by claim 2, wherein $R_5$ is hydrogen.

15. A compound as defined by claim 2, wherein $R_5$ is $-COOR_7$.

16. A compound as defined by claim 2, wherein $R_6$ is hydrogen.

17. A compound as defined by claim 2, wherein $R_6$ is $-COR_7$.

18. A compound as defined by claim 2, wherein $R_6$ is $-COOR_7$.

19. A compound as defined by claim 2 or 15, wherein $R_7$ is hydrogen.

20. A compound as defined by claim 2 or 15, wherein $R_7$ is $C_1-C_{20}$ alkyl.

21. A compound as defined by claim 2, wherein $R_7$ is $C_2-C_{20}$ alkenyl.

22. A compound as defined by claim 2, wherein $R_7$ is $C_5-C_7$ cycloalkyl.

23. A compound as defined by claim 2, wherein $R_7$ is phenyl.

24. A compound as defined by claim 2 or 15, wherein $R_7$ is benzyl.

25. A compound as defined by claim 2, wherein $R_8$ is hydrogen.

26. A compound as defined by claim 2, wherein $R_8$ is Cl or Br.

27. A compound as defined by claim 2, wherein $R_9$ is hydrogen.

28. A compound as defined by claim 2, wherein $R_9$ is $C_1-C_8$ alkyl.

29. A compound as defined by claim 1, having the structural formula (Ia)

wherein, $R_3$, $R_4$, $R_5$, $R_6$, X and the dotted lines are as defined in claim 1; and $R'_2$ is H, OH, $-OCO(C_1-C_{20}$ alkyl) or $-OCO(C_1-C_4$ alkyl)-phenyl.

30. A compound as defined by claim 29, wherein $R_6$ is hydrogen.

31. A compound as defined by claim 30, having the structural formula wherein $R'_3$ and $R'_4$ are each H or methyl; $R'_5$ is H or $-COOR'_7$ wherein $R'_7$ is H, $C_1-C_{20}$ alkyl or benzyl; =X' is =O or wherein $R'_3$, $R'_4$ and $R'_5$ are defined as above; and the dotted lines indicate the presence of a double bond at either the 4(5)- or the 5(6)-position.

32. A compound as defined by claim 31, wherein $R'_3$ and $R'_4$ are each H and $R'_5$ is $-COOR'_7$ wherein $R'_7$ is an alkyl group containing 1 to 12 carbon atoms.

33. A compound as defined by claim 30, wherein =X' is =O.

34. A compound as defined by claim 31 wherein =X' is wherein $R'_3$ and $R'_4$ are each H or methyl and $R'_5$ is H or $-COOR'_7$ wherein $R'_7$ is H, $C_1-C_{20}$ alkyl or benzyl.

35. A compound as defined by claim 32, wherein =X' is wherein the alkyl group contains 1 to 12 carbon atoms.

36. A compound as defined by claim 1, having the structural formula (II).

37. A compound as defined by claim 36, wherein $R_9$ is hydrogen.

38. A compound as defined by claim 36, wherein $R_9$ is $C_1$-$C_8$ alkyl.

39. A compound as defined by claim 36, wherein W is hydrogen.

40. A compound as defined by claim 36, wherein W is $C_1$-$C_{12}$ alkyl.

41. A compound as defined by claim 36, wherein W is $C_2$-$C_8$ alkenyl.

42. A compound as defined by claim 36, wherein W is $C_2$-$C_8$ alkynyl.

43. A compound as defined by claim 36, wherein Z is hydroxy.

44. A compound as defined by claim 36, wherein Z is —OCOR$_7$.

45. A compound as defined by claim 36, wherein Z is

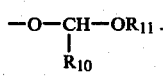

46. A compound as defined by claim 1, having the structural formula

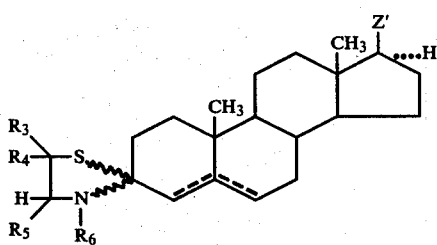

(IIa)

wherein $R_3$, $R_4$, $R_5$, $R_6$ and the dotted lines are as defined in claim 1; and Z' is OH, —OCO($C_1$-$C_{20}$ alkyl) or —OCO($C_1$-$C_4$ alkyl)-phenyl.

47. A compound as defined by claim 46, wherein $R_6$ is hydrogen.

48. A compound as defined by claim 47, having the structural formula

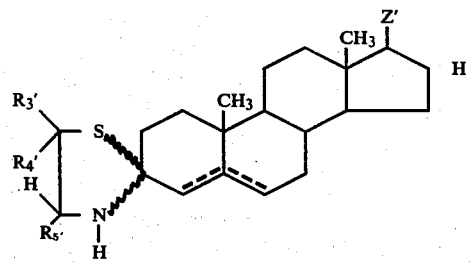

(IIb)

wherein $R'_3$ and $R'_4$ are each H or methyl; $R'_5$ is H or —COOR'$_7$ wherein R'$_7$ is H, $C_1$-$C_{20}$ alkyl or benzyl; Z' is OH, —OCO($C_1$-$C_{20}$ alkyl) or —OCO($C_1$-$C_4$ alkyl)-phenyl; and the dotted lines indicate the presence of a double bond at either the 4(5)- or the 5(6)-position.

49. A compound as defined by claim 48, wherein Z' is OH.

50. A compound as defined by claim 48, wherein R'$_3$ and R'$_4$ are each H and R'$_5$ is —COOR'$_7$ wherein R'$_7$ is an alkyl group containing 1 to 12 carbon atoms.

51. A compound as defined by claim 49, wherein R'$_3$ and R'$_4$ are each H and R'$_5$ is —COOR'$_7$ wherein R'$_7$ is an alkyl group containing 1 to 12 carbon atoms.

52. A compound as defined by claim 1, the same being 17β-(4″-ethoxycarbonyl-2″-methyl-1″,3″-thiazolidin-2″-yl)-4-androstene-3-spiro-2′-(4′-ethoxycarbonyl-1′,3′-thiazolidine).

53. A compound as defined by claim 1, the same being 17β-(4″-ethoxycarbonyl-2″-methyl-1″,3″-thiazolidin-2″-yl)-5-androstene-3-spiro-2′-(4′-ethoxycarbonyl-1′,3′-thiazolidine).

54. A compound as defined by claim 1, the same being 17β-(4″-butyloxycarbonyl-2″-methyl-1″,3″-thiazolidin-2″-yl-4-androstene-3-spiro-2′-(4′-butyloxycarbonyl-1′,3′-thiazolidine).

55. A compound as defined by claim 1, the same being 17β-(4″-butyloxycarbonyl-2″-methyl-1″,3″-thiazolidin-2″-yl)-5-androstene-3-spiro-2′-(4′-butyloxycarbonyl-1′,3′-thiazolidine).

56. A compound as defined by claim 1, the same being 17β-(4″-hexyloxycarbonyl-2″-methyl-1″,3″-thiazolidin-2″-yl)-4-androstene-3-spiro-2′-(4′-hexyloxycarbonyl-1′,3′-thiazolidine).

57. A compound as defined by claim 1, the same being 17β-(4″-hexyloxycarbonyl-2″-methyl-1″,3″-thiazolidin-2″-yl)-5-androstene-3-spiro-2′-(4′-hexyloxycarbonyl-1′,3′-thiazolidine).

58. A compound as defined by claim 1, the same being 17β-(4″-decyloxycarbonyl-2″-methyl-1″,3″-thiazolidin-2″-yl)-4-androstene-3-spiro-2′-(4′-decyloxycarbonyl-1′,3′-thiazolidine).

59. A compound as defined by claim 1, the same being 17β-(4″-decyloxycarbonyl-2″-methyl-1″,3″-thiazolidin-2″-yl)-5-androstene-3-spiro-2′-(4′-decyloxycarbonyl-1′,3′-thiazlidine).

60. A compound as defined by claim 1, the same being 17β-(4″-tert-butyloxycarbonyl-2″-methyl-1″,3″-thiazolidin-2″-yl)-4-androstene-3-spiro-2′-(4′-tert-butyloxycarbonyl-1′,3′-thiazolidine).

61. A compound as defined by claim 1, the same being 17β-(4″-tert-butyloxycarbonyl-2″-methyl-1″,3″-thiazolidin-2″-yl)-5-androstene-3-spiro-2′-(4′-tert-butyloxycarbonyl-1′,3′-thiazolidine).

62. A compound as defined by claim 1, the same being 17β-(4″-benzyloxycarbonyl-2″-methyl-1″,3″-thiazolidin-2″-yl-4-androstene-3-spiro-2′-(4′-benzyloxycarboxyl-1′,3′-thiazolidine).

63. A compound as defined by claim 1, the same being 17β-(4″-benzyloxycarbonyl-2″-methyl-1″,3″-thiazolidin-2″-yl)-5-androstene-3-spiro-2′-(4′-benzyloxycarbonyl-1′,3′-thiazoline).

64. A compound as defined by claim 1, the same being 17β-(4″-isopropyloxycarbonyl-2″-methyl-1″,3″-thiazolidin-2″-yl)-4-androstene-3-spiro-2′-(4′-isopropyloxycarbonyl-1′,3′-thiazolidine).

65. A compound as defined by claim 1, the same being 17β-(4″-isopropyloxycarbonyl-2″-methyl-1″,3″-thiazolidin-2″-yl)-5-androstene-3-spiro-2′-(4′-ispropyloxycarbonyl-1′,3′-thiazolidine).

66. A compound as defined by claim 1, the same being 4-pregnene-3-spiro-2′-(4′-ethoxycarbonyl-1′,3′-thiazolidine)-20-one.

67. A compound as defined by claim 1, the same being 5-pregnene-3-spiro-2′-(4′-ethoxycarbonyl-1′,3′-thiazolidine)-20-one.

68. A compound as defined by claim 1, the same being 4-pregnene-3-spiro-2′-(4′-butyloxycarboxyl-1′,3′-thiazolidine)-20-one.

69. A compound as defined by claim 1, the same being 5-pregnene-3-spiro-2′-(4′-butyloxycarbonyl-1′,3′-thiazolidine)-20-one.

70. A compound as defined by claim 1, the same being 4-pregnene-3-spiro-2'-(4'-hexyloxycarbonyl-1',3'-thiazolidine)-20-one.

71. A compound as defined by claim 1, the same being 5-pregnene-3-spiro-2'-(4'-hexyloxycarbonyl-1',3'-thiazolidine)-20-one.

72. A compound as defined by claim 1, the same being 4-pregnene-3-spiro-2'-(4'-decyloxycarbonyl-1',3'-thiazolidine)-20-one.

73. A compound as defined by claim 1, the same being 5-pregnene-3-spiro-2'-(4'-decyloxycarbonyl-1',3'-thiazolidine)-20-one.

74. A compound as defined by claim 1, the same being 4-pregnene-3-spiro-2'-(4'-tert-butyloxycarbonyl-1',3'-thiazolidine)-20-one.

75. A compound as defined by claim 1, the same being 5-pregnene-3-spiro-2'-(4'-tert-butyloxycarbonyl-1',3'-thiazolidine)-20-one.

76. A compound as defined by claim 1, the same being 4-pregnene-3-spiro-2'-(4'-benzyloxycarbonyl-1',3'-thiazolidine)-20-one.

77. A compound as defined by claim 1, the same being 5-pregnene-3-spiro-2'-(4'-benzyloxycarbonyl-1',3'-thiazolidine)-20-one.

78. A compound as defined by claim 1, the same being 4-pregnene-3-spiro-2'-(4'-isopropyloxycarbonyl-1',3'-thiazolidine)-20-one.

79. A compound as defined by claim 1, the same being 5-pregnene-3-spiro-2'-(4'-isopropyloxycarbonyl-1',3'-thiazolidine)-20-one.

80. A compound as defined by claim 1, the same being 17$\beta$-(4''-ethoxycarbonyl-2'',5'',5''-trimethyl-1'',3''-thiazolidin-2''-yl)-4-androstene-3-spiro-2'-(4'-ethoxycarbonyl-5',5'-dimethyl-1',3'-thiazolidine).

81. A compond as defined by claim 1, the same being 17$\beta$-(4''-ethoxycarbonyl-2'',5'',5''-trimethyl-1'',3''-thiazolidin-2''-yl)-5-androstene-3-spiro-2'-(4'-ethoxycarbonyl-5',5'-dimethyl-1',3'-thiazolidine).

82. A compound as defined by claim 1, the same being 17$\beta$-(4''-hexyloxycarbonyl-2'',5'',5''-trimethyl-1'',3''-thiazolidin-2''-yl)-4-androstene-3-spiro-2'-(4'-hexyloxycarbonyl-5',5'-dimethyl-1',3'-thiazolidine).

83. A compound as defined by claim 1, the same being 17$\beta$-(4''-hexyloxycarbonyl-2'',5'',5''-trimethyl-1'',3''-thiazolidin-2''-yl)-5-androstene-3-spiro-2'-(4'-hexyloxycarbonyl-5',5'-dimethyl-1',3'-thiazolidine).

84. A compound as defined by claim 1, the same being 17$\beta$-(4''-butyloxycarbonyl-2'',5'',5''-trimethyl-1'',3''-thiazolidin-2''-yl)-4-androstene-3-spiro-2'-(4'-butyloxycarbonyl-5',5'-dimethyl-1',3'-thiazolidine).

85. A compound as defined by claim 1, the same being 17$\beta$-(4''-butyloxycarbonyl-2'',5'',5''-trimethyl-1'',3''-thiazolidin-2''-yl)-5-androstene-3-spiro-2'-(4'-butyloxycarbonyl-5',5'-dimethyl-1',3'-thiazolidine).

86. A compound as defined by claim 1, the same being 6$\alpha$-chloro-17$\beta$-(4''-ethoxycarbonyl-2''-methyl-1'',3''-thiazolidin-2''-yl)-4-androstene-3-spiro-2'-(4'-ethoxycarbonyl-1',3'-thiazolidine).

87. A compound as defined by claim 1, the same being 6$\alpha$-chloro-17$\beta$-(4''-ethoxycarbonyl-2''-methyl-1'',3''-thiazolidin-2''-yl)-5-androstene-3-spiro-2'-(4'-ethoxycarbonyl-1',3'-thiazolidine).

88. A compound as defined by claim 1, the same being 17$\beta$-(4''-butyloxycarbonyl-2''-methyl-1'',3''-thiazolidin-2''-yl)-6$\alpha$-chloro-4-androstene-3-spiro-2'-(4'-butyloxycarbonyl-1',3'-thiazolidine).

89. A compound as defined by claim 1, the same being 17$\beta$-(4''-butyloxycarbonyl-2''-methyl-1'',3''-thiazolidin-2''-yl)-6$\alpha$-chloro-5-androstene-3-spiro-2'-(4'-butyloxycarbonyl-1',3'-thiazolidine).

90. A compound as defined by claim 1, the same being 6$\alpha$-chloro-17$\beta$-(4''-hexyloxycarbonyl-2''-methyl-1'',3''-thiazolidin-2''-yl)-4-androstene-3-spiro-2'-(4'-hexyloxycarbonyl-1',3'-thiazolidine).

91. A compound as defined by claim 1, the same being 6$\alpha$-chloro-17$\beta$-(4''-hexyloxycarbonyl-2''-methyl-1'',3''-thiazolidin-2''-yl)-5-androstene-3-spiro-2'-(4'-hexyloxycarbonyl-1',3'-thiazolidine).

92. A compound as defined by claim 1, the same being 17$\alpha$-acetyloxy-17$\beta$-(4''-ethoxycarbonyl-2''-methyl-1'',3''-thiazolidin-2''-yl)-6$\alpha$-methyl-4-androstene-3-spiro-2'-(4'-ethoxycarbonyl-1',3'-thiazolidine).

93. A compound as defined by claim 1, the same being 17$\alpha$-acetyloxy-17$\beta$-(4''-ethoxycarbonyl-2''-methyl-1'',3''-thiazolidin-2''-yl)-6$\alpha$-methyl-5-androstene-3-spiro-2'-(4'-ethoxycarbonyl-1',3'-thiazolidine).

94. A compound as defined by claim 1, the same being 17$\alpha$-acetyloxy-17$\beta$-(4''-butyloxycarbonyl-2''-methyl-1'',3''-thiazolidin-2''-yl)-6$\alpha$-methyl-4-androstene-3-spiro-2'-(4'-butyloxycarbonyl)-1',3'-thiazolidine).

95. A compound as defined by claim 1, the same being 17$\alpha$-acetyloxy-17$\beta$-(4''-butyloxycarbonyl-2''-methyl-1'',3''-thiazolidin-2''-yl)-6$\alpha$-methyl-5-androstene-3-spiro-2'-(4'-butyloxycarbonyl-1',3'-thiazolidine).

96. A compound as defined by claim 1, the same being 17$\alpha$-acetyloxy-17$\beta$-(4''-hexyloxycarbonyl-2''-methyl-1'',3''-thiazolidin-2''-yl)-6$\alpha$-methyl-4-androstene-3-spiro-2'-(4'-hexyloxycarbonyl-1',3'-thiazolidine).

97. A compound as defined by claim 1, the same being 17$\alpha$-acetyloxy-17$\beta$-(4''-hexyloxycarbonyl-2''-methyl-1'',3''-thiazolidin-2''-yl)-6$\alpha$-methyl-5-androstene-3-spiro-2'-(4'-hexyloxycarbonyl-1',3'-thiazolidine).

98. A compound as defined by claim 1, the same being 17$\alpha$-acetyloxy-17$\beta$-(4''-ethoxycarbonyl-2''-methyl-1'',3''-thiazolidin-2''-yl)-9$\alpha$-fluoro-4-androstene-3-spiro-2'-(4'-ethoxycarbonyl-1',3'-thiazolidine).

99. A compound as defined by claim 1, the same being 17$\alpha$-acetyloxy-17$\beta$-(4''-ethoxycarbonyl-2''-methyl-1'',3''-thiazolidin-2''-yl)-9$\alpha$-fluoro-5-androstene-3-spiro-2'-(4'-ethoxycarbonyl-1',3'-thiazolidine).

100. A compound as defined by claim 1, the same being 17$\alpha$-acetyloxy-17$\beta$-(4''-butyloxycarbonyl-2''-methyl-1'',3''-thiazolidin-2''-yl)-9$\alpha$-fluoro-4-androstene-3-spiro-2'-(4'-butyloxycarbonyl-1',3'-thiazolidine).

101. A compound as defined in claim 1, the same being 17$\alpha$-acetyloxy-17$\beta$-(4''-butyloxycarbonyl-2''-methyl-1'',3''-thiazolidin-2''-yl)-9$\alpha$-fluoro-5-androstene-3-spiro-2'-(4'-butyloxycarbonyl-1',3'-thiazolidine).

102. A compound as defined by claim 1, the same being 17$\alpha$-acetyloxy-9$\alpha$-fluoro-17$\beta$-(4''-hexyloxycarbonyl-2''-methyl-1'',3''-thiazolidin-2''-yl)-4-androstene-3-spiro-2'-(4'-hexyloxycarbonyl-1',3'-thiazolidine).

103. A compound as defined by claim 1, the same being 17$\alpha$-acetyloxy-9$\alpha$-fluoro-17$\beta$-(4''-hexyloxycarbonyl-2''-methyl-1'',3''-thiazolidin-2''-yl)-5-androstene-3-spiro-2'-(4'-hexyloxycarbonyl-1',3'-thiazolidine).

104. A compound as defined by claim 1, the same being 17$\alpha$-acetyloxy-6$\alpha$-methyl-4-pregnene-3-spiro-2'-(4'-ethoxycarbonyl-1',3'-thiazolidine)-20-one.

105. A compound as defined by claim 1, the same being 17$\alpha$-acetyloxy-6$\alpha$-methyl-5-pregnene-3-spiro-2'-(4'-ethoxycarbonyl-1',3'-thiazolidine)-20-one.

106. A compound as defined by claim 1, the same being 17$\alpha$-acetyloxy-6$\alpha$-methyl-4-pregnene-3-spiro-2'-(4'-hexyloxycarbonyl-1',3'-thiazolidine)-20-one.

107. A compound as defined by claim 1, the same being 17α-acetyloxy-6α-methyl-5-pregnene-3-spiro-2'-(4'-hexyloxycarbonyl-1',3'-thiazolidine)-20-one.

108. A compound as defined by claim 1, the same being 17α-acetyloxy-6α-methyl-4-pregnene-3-spiro-2'-(4'-isopropyloxycarbonyl-1',3'-thiazolidine)-20-one.

109. A compound as defined by claim 1, the same being 17α-acetyloxy-6α-methyl-5-pregnene-3-spiro-2'-(4'-isopropyloxycarbonyl-1',3'-thiazolidine)-20-one.

110. A compound as defined by claim 1, the same being 17β-[3''',4'''-di(ethoxycarbonyl)-2'''-methyl-1''',3'''-thiazolidin-2'''-yl]-4-androstene-3-spiro-2'-[3',4'-di(ethoxycarbonyl)-1',3'-thiazolidine].

111. A compound as defined by claim 1, the same being 17β-[3''',4'''-di(ethoxycarbonyl)-2'''-methyl-1''',3'''-thiazolidin-2'''-yl]-5-androstene-3-spiro-2'-[3',4'-di(ethoxycarbonyl)-1',3'-thiazolidine].

112. A compound as defined by claim 1, the same being 17β-(4'''-carboxy-2''',5''',5'''-trimethyl-1''',3'''-thiazolidin-2'''-yl)-4-androstene-3-spiro-2'-(4'-carboxy-5',5'-dimethyl-1',3'-thiazolidine).

113. A compound as defined by claim 1, the same being 17β-(4'''-carboxy-2''',5''',5'''-trimethyl-1''',3'''-thiazolidin-2'''-yl)-5-androstene-3-spiro-2'-(4'-carboxy-5',5'-dimethyl-1',3'-thiazolidine).

114. A compound as defined by claim 1, the same being 17α-ethynyl-4-androstene-3-spiro-2'-(4'-ethoxycarbonyl-1',3'-thiazolidine)-17β-ol.

115. A compound as defined by claim 1, the same being 17α-ethynyl-5-androstene-3-spiro-2'-4'-ethoxycarbonyl-1',3'-thiazolidine)-17β-ol.

116. A compound as defined by claim 1, the same being 17α-ethynyl-19-nor-4-androstene-3-spiro-2'-(4'-ethoxycarbonyl-1',3'-thiazolidine)-17β-ol.

117. A compound as defined by claim 1, the same being 17α-ethynyl-19-nor-5-androstene-3-spiro-2'-(4'-ethoxycarbonyl-1',3'-thiazolidine)-17β-ol.

118. A compound as defined by claim 1, the same being 4-androstene-3-spiro-2'-(4'-carboxy-1',3'-thiazolidine)-17β-ol.

119. A compound as defined by claim 1, the same being 5-androstene-3-spiro-2'-(4'-carboxy-1',3'-thiazolidine)-17β-ol.

120. A compound as defined by claim 1, the same being 4-androstene-3-spiro-2'-(4'-ethoxycarbonyl-1',3'-thiazolidine)-17β-ol.

121. A compound as defined by claim 1, the same being 5-androstene-3-spiro-2'-(4'-ethoxycarbonyl-1',3'-thiazolidine)-17β-ol.

122. A compound as defined by claim 1, the same being 4-androstene-3-spiro-2'-(4'-hexyloxycarbonyl-1',3'-thiazolidine)-17β-ol.

123. A compound as defined by claim 1, the same being 4-androstene-3-spiro-2'-(4'-hexyloxycarbonyl-1',3'-thiazolidine)-17β-ol.

124. A compound as defined by claim 1, the same being 5-androstene-3-spiro-2'-(4'-ethoxycarbonyl-1',3'-thiazolidine)-17β-ol.

125. A compound as defined by claim 1, the same being 4-androstene-3-spiro-2'-(4'-butyloxycarbonyl)-5',5'-dimethyl-1',3'-thiazolidine)-17β-ol.

126. A compound as defined by claim 1, the same being 5-androstene-3-spiro-2'-(4'-butyloxycarbonyl)-5',5'-dimethyl-1',3'-thiazolidine)-17β-ol.

127. A compound as defined by claim 1, the same being 4-androstene-3-spiro-2'-(4'-ethoxycarbonyl-1',3'-thiazolidine)-17β-ol 17-propionate.

128. A compound as defined by claim 1, the same being 5-androstene-3-spiro-2'-(4'-ethoxycarbonyl-1',3'-thiazolidine)-17β-ol 17-propionate.

129. A compound as defined by claim 1, the same being 19-nor-4-androstene-3-spiro-2'-(4'-ethoxycarbonyl-1',3'-thiazolidine)-17β-ol 17-propionate.

130. A compound as defined by claim 1, the same being 19-nor-5-androstene-3-spiro-2'-(4'-ethoxycarbonyl-1',3'-thiazolidine)-17β-ol 17-propionate.

131. A compound as defined by claim 1, the same being 19-nor-4-androstene-3-spiro-2'-(4'-ethoxycarbonyl-1',3'-thiazolidine)-17β-ol 17-adamantyl carboxylate.

132. A compound as defined by claim 1, the same being 19-nor-5-androstene-3-spiro-2'-(4'-ethoxycarbonyl-1',3'-thiazolidine)-17β-ol 17-adamantyl carboxylate.

133. A compound as defined by claim 1, the same being 19-nor-4-androstene-3-spiro-2'-(4'-ethoxycarbonyl-1',3'-thiazolidine)-17β-ol 17-phenylpropionate.

134. A compound as defined by claim 1, the same being 19-nor-5-androstene-3-spiro-2'-(4'-ethoxycarbonyl-1',3'-thiazolidine)-17β-ol 17-phenylpropionate.

135. A compound as defined by claim 1, the same being 4-androstene-3-spiro-2'-(4'-ethoxycarbonyl-5',5'-dimethyl-1',3'-thiazolidine)-17β-ol.

136. A compound as defined by claim 1, the same being 5-androstene-3-spiro-2'-(4'-ethoxycarbonyl-5',5'-dimethyl-1',3'-thiazolidine)-17β-ol.

137. A compound as defined by claim 1, the same being 17β-propionyloxy-4-androstene-3-spiro-2'-(4'-ethoxycarbonyl-1',3'-thiazolidine).

138. A compound as defined by claim 1, the same being 17β-propionyloxy-5-androstene-3-spiro-2'-(4'-ethoxycarbonyl-1',3'-thiazolidine).

139. A compound as defined by claim 1, the same being 17β-(4'''-methoxycarbonyl-2'''-methyl-1''',3'''-thiazolidine-2'''-yl)-4-androstene-3-spiro-2'-(4'-methoxycarbonyl-1',3'-thiazolidine).

140. A compound as defined by claim 1, the same being 17β-(4'''-methoxycarbonyl-2'''-methyl-1''',3'''-thiazolidin-2'''-yl)-5-androstene-3-spiro-2'-(4'-methoxycarbonyl-1',3'-thiazolidine).

141. A compound as defined by claim 1, the same being 17β-propionyloxy-5-androstene-3-spiro-2'-(1',3'-thiazolidine).

142. A compound as defined by claim 1, the same being 17β-propionyloxy-4-androstene-3-spiro-2'-(1',3'-thiazolidine).

143. A compound as defined by claim 1, the same being 5-pregnene-3-spiro-2'-(1',3'-thiazolidine)-20-one.

144. A compound as defined by claim 1, the same being 4-pregnene-3-spiro-2'-(1',3'-thiazolidine)-20-one.

* * * * *